United States Patent [19]

Fujimura et al.

[11] Patent Number: 4,826,431
[45] Date of Patent: May 2, 1989

[54] MEDICAL LASER HANDPIECE

[75] Inventors: Yoshisaburo Fujimura, Uji; Kenzo Kataoka, Otsu; Akira Yuba, Uji; Hiroshi Komori, Kyoto, all of Japan

[73] Assignee: Kabushiki Kaisha Morita Seisakusho, Kyoto, Japan

[21] Appl. No.: 61,868

[22] Filed: Jun. 11, 1987

[30] Foreign Application Priority Data

Jun. 12, 1986 [JP] Japan .................. 61-089749
Nov. 25, 1986 [JP] Japan .................. 61-181622
Nov. 25, 1986 [JP] Japan .................. 61-181623
Nov. 25, 1986 [JP] Japan .................. 61-181624

[51] Int. Cl.⁴ ............................................. A61C 3/00
[52] U.S. Cl. ...................................... 433/29; 433/80; 433/215; 128/303.1
[58] Field of Search .................. 433/29, 114, 80, 215, 433/229; 128/303.1

[56] References Cited

U.S. PATENT DOCUMENTS

| 4,503,853 | 3/1985 | Ota et al. ................ 128/303.1 |
| 4,604,992 | 8/1986 | Sato ......................... 128/303.1 |
| 4,608,980 | 9/1986 | Aihara ..................... 128/303.1 |
| 4,617,926 | 10/1986 | Sutton ..................... 128/303.1 |
| 4,619,612 | 10/1986 | Weber et al. ............ 433/29 |
| 4,648,838 | 3/1987 | Schlachter .............. 433/29 |
| 4,676,242 | 6/1987 | Doi ........................... 128/303.1 |

FOREIGN PATENT DOCUMENTS 2033649  5/1980  United Kingdom ............ 128/303.1

Primary Examiner—John J. Wilson
Attorney, Agent, or Firm—Koda and Androlia

[57] ABSTRACT

A medical laser handpiece comprising a grip body, a semiconductor laser generator disposed in the grip body and an irradiation nozzle which is detachably cross-connected to the head of the grip body at an angle and includes a laser light transmitting means from the semiconductor laser generator. With this laser handpiece, an operator can accurately and easily treat even relatively small and complicated shaped teeth and periodontal sections in the mouth. In addition to a structure capable of irradiating laser light and a structure capable of cooling the semiconductor generator, this invention also includes a structure capable of jetting air, water and a mist of air and water, and a structure capable of reducing irradiation loss of laser light.

7 Claims, 10 Drawing Sheets

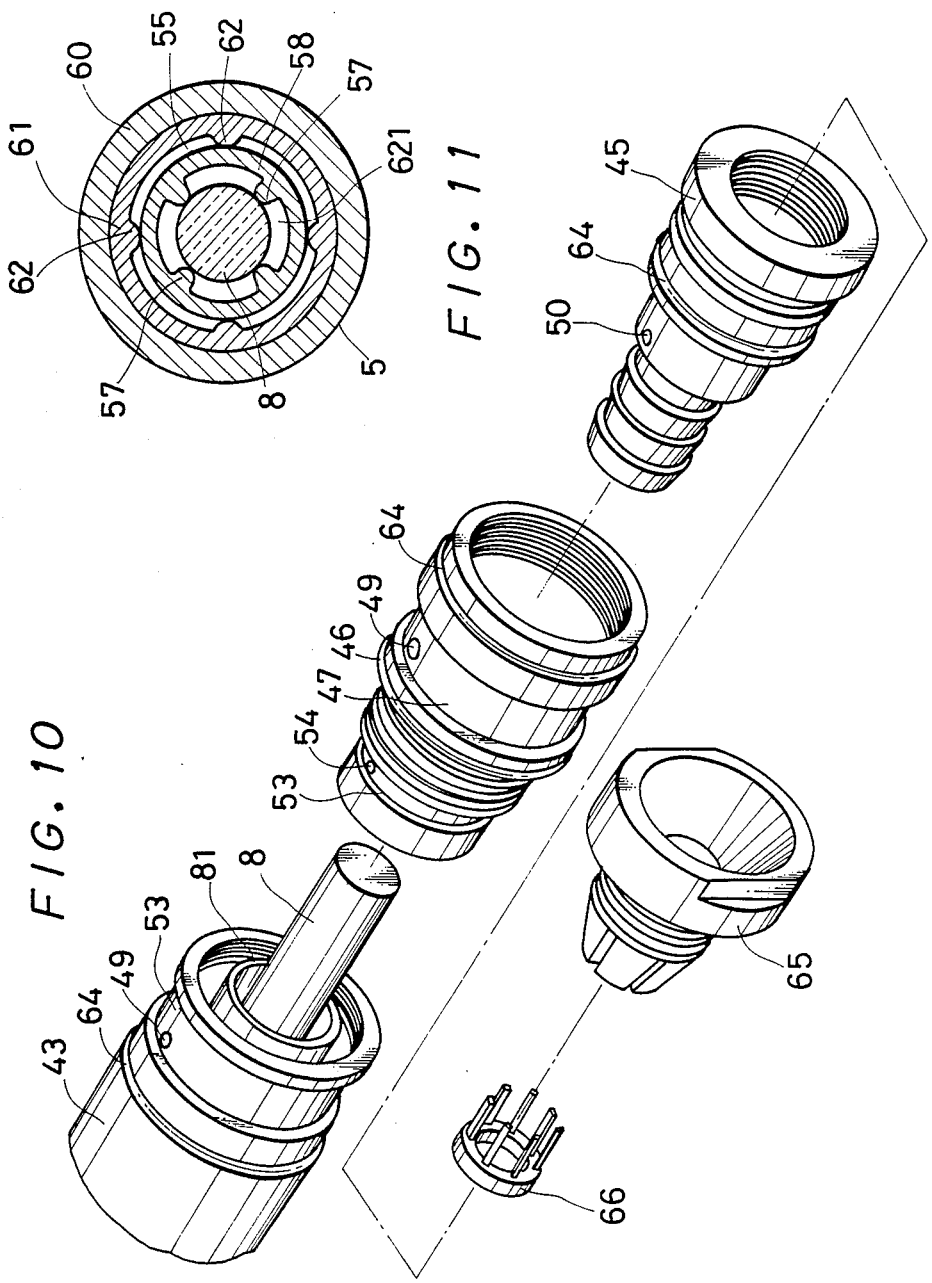

MEDICAL LASER HANDPIECE

BACKGROUND OF THE INVENTION

1. Field of the Invention

The present invention relates to a medical handpiece equipped with a semiconductor laser generator which generates laser light in order to accurately irradiate laser light to treatment portions according to treatment purposes such as antiphlogistic treatment, odynolysis, acceleration of healing and hardening of optical polymerization substances.

2. Prior Art

A laser handpiece requiring a relatively large laser generator such as YAG laser generator or a $CO_2$ laser generator and a laser handpiece including such a small semiconductor generator as used in the present invention are known as conventional medical laser handpieces. In the case of the former handpiece, the laser light generated by the laser generator is transmitted to the handpiece through a laser light transmitting means or by using a mirror or a manipulator. In the case of the latter handpiece, a semiconductor laser generator is built in the handpiece body or grip as disclosed by Japanese Provisional Patent Publication No. 60-24832.

In the case when a laser handpiece is used for treatment of relatively small and complicated shaped teeth and periodontal sections in the mouth, the end or head of the hand-piece body must be turned while it is held so that laser light can be irradiated close to the teeth and periodontal sections.

The conventional medical laser handpiece which includes a semiconductor laser generator in its grip is made to irradiate laser light to relatively wide and flat portions such as human body surfaces. Although the laser light irradiated from the semiconductor laser generator is transmitted to an affected portion via a mirror for example, it is difficult for a dentist to look at the affected portion since the laser light irradiation port is provided too close to the grip. When irradiating laser light into an innermost affected portion such as a molar in the mouth, the grip interferes with the wall of the mouth, preventing treatment.

SUMMARY OF THE INVENTION

It is therefore an object of the present invention to provide an improved medical laser handpiece wherein a semiconductor laser generator is included in its head and an irradiation nozzle is detachably cross-connected to the handpiece head so that laser light can be accurately irradiated from the end port of the irradiation nozzle to an affected dental treatment portion, thus eliminating the above-mentioned defects of the conventional medical laser handpieces. This general-purpose handpiece of the present invention is referred to as type I for convenience of explanation.

The present invention also provides another type of the above-mentioned handpiece (hereafter referred to as type II) which has a function to reduce heat generation and output loss of the laser generator. A third type (hereafter referred to as type III) has a function to jet air, water or mist of water and air. A fourth type (hereafter referred to as type IV) has a function to prevent leakage of laser light at the transmission path between the laser generator and the laser light transmitting means. The present invention also provides types II, III and IV which are more efficient than type I.

BRIEF DESCRIPTION OF THE DRAWINGS

The embodiment of the present invention (types I, II, III and IV) are detailed referring to the accompanying drawings.

FIG. 10 is an exploded perspective view of section D of FIG. 7; and

FIG. 11 is a sectional view taken on line E—E in FIG. 9.

DETAILED DESCRIPTION OF THE INVENTION

Type I of the present invention is explained referring to FIGS. 1 to 5.

Figure 1:
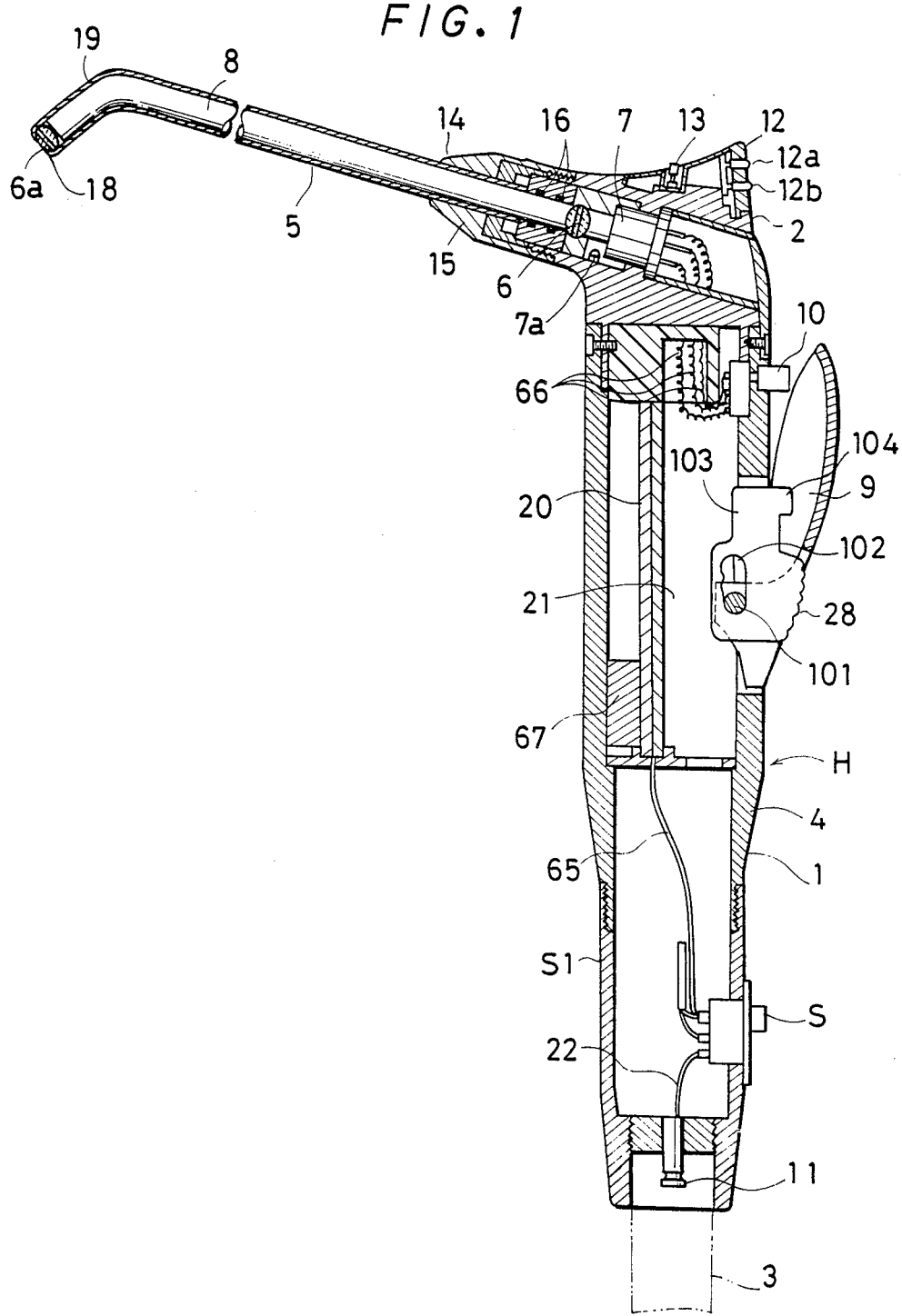
FIG. 1 is a vertical sectional side view illustrating an embodiment of type I of the present invention.

As shown in FIG. 1, handpiece H includes a grip body 1, a grip head 2 and an irradiation nozzle 5. The irradiation nozzle 5 is detachably connected to the grip head 2 of the long grip body 1 at an angle, intersecting the axis of the grip body 1. An inwardly bent section 19 is provided at the end of the irradiation nozzle 5 so that the end of the irradiation nozzle 5 can face any affected portion which is difficult to reach (for example, the inside of a tooth). If the affected portion can be treated using a straight irradiation nozzle, it is not necessary to provide such a bent section.

A sleeve joint S1 is screwed over the lower end of the grip body 1. This joint S1 has an exposed power switch S and includes a connection plug 11 at its lower end. A connection hose 3 including a connection plug (not shown) which mates with the connection plug 11 is connected to the lower end of the joint S1. The power switch S and a control mechanism 21 including a control PC (printed circuit) board 20 are connected by a conducting wire 65. The control mechanism 21, an irradiation switch 10 and a semiconductor laser generator 7 are connected by a conducting wire 66. The control mechanism 21 is just roughly illustrated for convenience of explanation. Using the above-mentioned structure, electric power from a power source (not shown) is supplied to the irradiation switch 10 via the control mechanism 21 when the power switch S is turned on. When the irradiation switch 10 is turned on, electric power is supplied to the semiconductor laser generator 7.

The irradiation switch 10 is turned on when the head of the switch 10 is pressed by the hinge action of a control lever 9 which is pivotably connected to the grip body 1 via a pin 101 and provided over the switch 10. The irradiation switch 10 is turned off when the control lever 9 is returned to release the switch 10.

Figure 5:
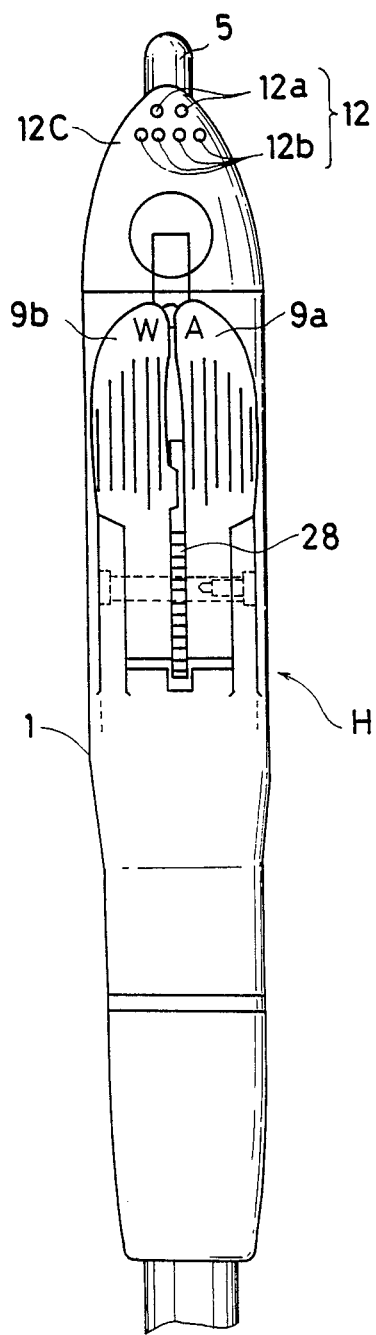
FIG. 5 is plan view of the third embodiment.

The control lever 9 is for example pivotably connected and protrudes beyond a handpiece cover 4 as shown in FIG. 1 and has for example a locking mechanism including a lock mechanism 28 as shown in FIG. 5 so that the control lever 9 can be locked when necessary.

In the lock mechanism 28, a slider knob 103 having a slot 102 into which the pin 101 is fit is provided under the control lever 9. When the pin 101 is positioned at the bottom of the slot 102 as shown in FIG. 1, the locking pawl 104 is separated from the lever 9. When the slide knob 103 is lowered by a finger and the pin 101 contacts the top of the slot 102 (this condition is not shown), the locking pawl 104 contacts the lower inside section of the control lever 9 to prevent the hinge action of the control lever 9. In this way, this locking mechanism 28 prevents the irradiation switch 10 from being turned on.

In the head grip 2, the semiconductor laser generator 7 comprising for example AlGaInP or AlGaAs is disposed along the axis of the irradiation nozzle 5 connected to the grip head 2 as shown in FIG. 1. In the irradiation nozzle 5, a laser light transmitting means 8 such as an optical fiber is disposed to transmit laser light generated from the semiconductor laser generator 7. Inside the end port 18 of the nozzle, a condenser lens 6a is disposed to condense the transmitted laser light.

In the grip head 2, a convergent lens 6, which converges laser light generated from the semiconductor laser generator 7 into a laser beam which contacts the base end of the laser light transmitting means 8 in the nozzle 5 is provided. A clearance is given between the convergent lens 6 and the semiconductor laser generator 7.

Figure 2:
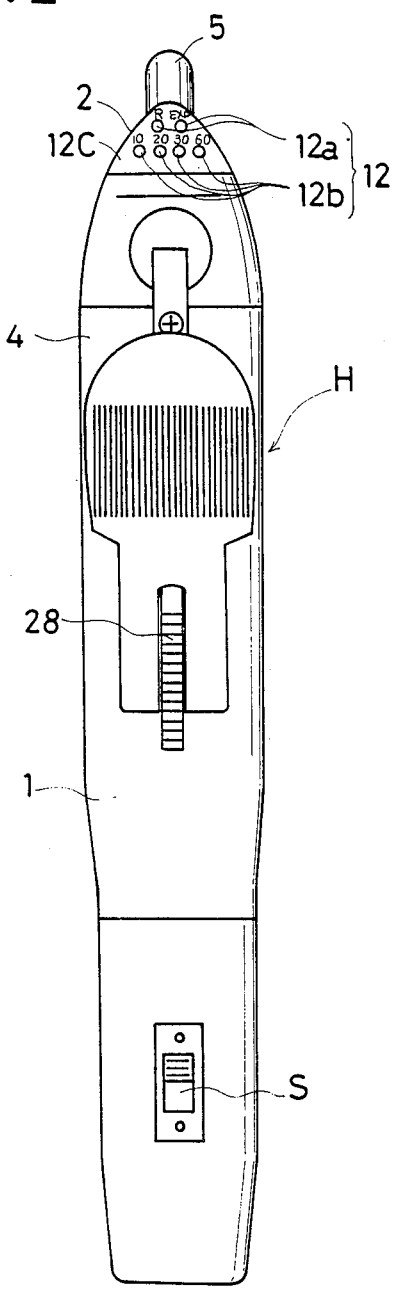
FIG. 2 is a plan view of the embodiment type I.

A display means 12 is disposed on the top of the grip head 2 as shown in FIG. 2. When the power switch S is turned on, the lamp R of the 12a section of the display means 12 lights to indicate that irradiation is ready. When the irradiation switch 10 is turned on, the EXP lamp of the 12a section lights to indicate that irradiation is being performed. The lamps of the 12b section of the display means 12 are used to indicate irradiation time. The lamp corresponding to the desired irradiation time mode selected by the control mode selection switch 13 lights to indicate the selected mode. When the time preset in a timer is reached, the lamp automatically turns off. At a proper position of the laser irradiation path in the grip head 2, a laser detector 7a is disposed. The laser irradiation signal detected by this detector 7a is transmitted to a buzzer 67 and the buzzer 67 generates sound composed of for example two tone to notify the operator of laser irradiation. When the power switch S is turned on, the buzzer 67 generates different sound to notify the operator of the standby condition.

Figure 3:
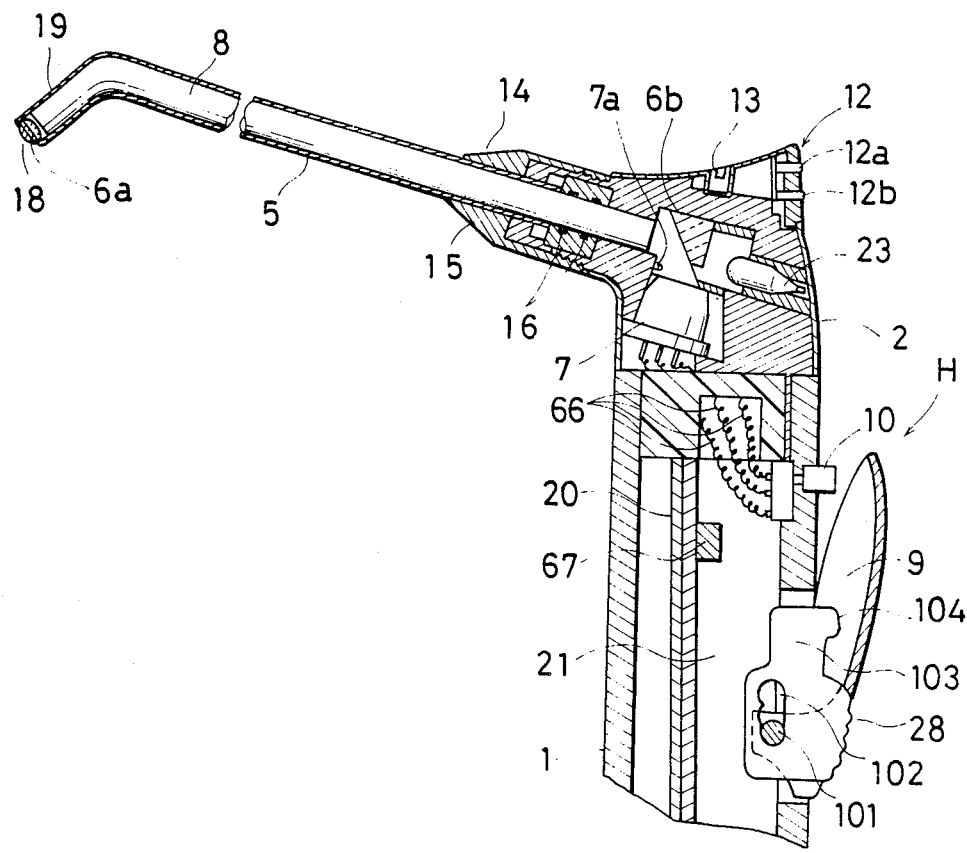
FIG. 3 is a vertical sectional side view illustrating the major section of another embodiment of type I.

Although the semiconductor laser generator 7 located inside the grip head 2 is positioned on the axis of the irradiation nozzle 5 connected to the grip head 2 as described above, the semiconductor laser generator 7 can have such a structure as that shown in FIG. 3. Referring to FIG. 3, the semiconductor laser generator 7 is disposed in the grip body 1 at a position where the axis of the semiconductor laser generator 7 crosses the axis of the irradiation nozzle 5, and a light-transmission reflective lens 6b is disposed facing the semiconductor laser generator 7 so that the laser generated from the semiconductor laser 7 is reflected by the lens 6b and transmitted via the laser light transmitting means 8 of the irradiation nozzle 5 and the condenser lens 6a located inside the nozzle end port 18 to the outside of the nozzle.

In this case, by disposing a lighting means 23 such as a halogen lamp or an incandescent lamp on the axis of the irradiation nozzle 5 connected to the grip head 2, by transmitting light from the lighting means 23 via the lens 6b and by leading the light to the laser light transmitting means 8 in the irradiation nozzle 5, the irradiation condition of the non-visible laser can be clearly seen using the light from the lighting means 23 and the condition of a treatment portion can be accurately confirmed. As a matter of course, the lighting means 23 can be used independently of a laser. Although the lighting means 23 is disposed on the axis of the nozzle 5 in the above-mentioned case, the semiconductor laser generator 7 and the lighting means 23 can be disposed at a position other than those described above inside the grip body 1 using a known prism or an optical part.

The irradiation nozzle 5 is rotatably and detachably connected to the grip head 2 via O-rings 16. More particularly, a cover nut 15, in which the irradiation nozzle 5 is inserted, is screwed over the connection section 14 of the grip head 2. The irradiation nozzle 5 is rotatably and detachably supported by the O-rings 16. In addition, the O-rings 16 prevent leakage of laser light. Therefore, the irradiation nozzle 5 can be removed and replaced with a new one when it is necessary to replace the nozzle 5 according to the condition at a treatment portion. Furthermore, the end port 18 of the nozzle 5 can be directed to any treatment portion by rotating the nozzle 5 in the desired direction while the nozzle 5 remains installed.

Figure 4:
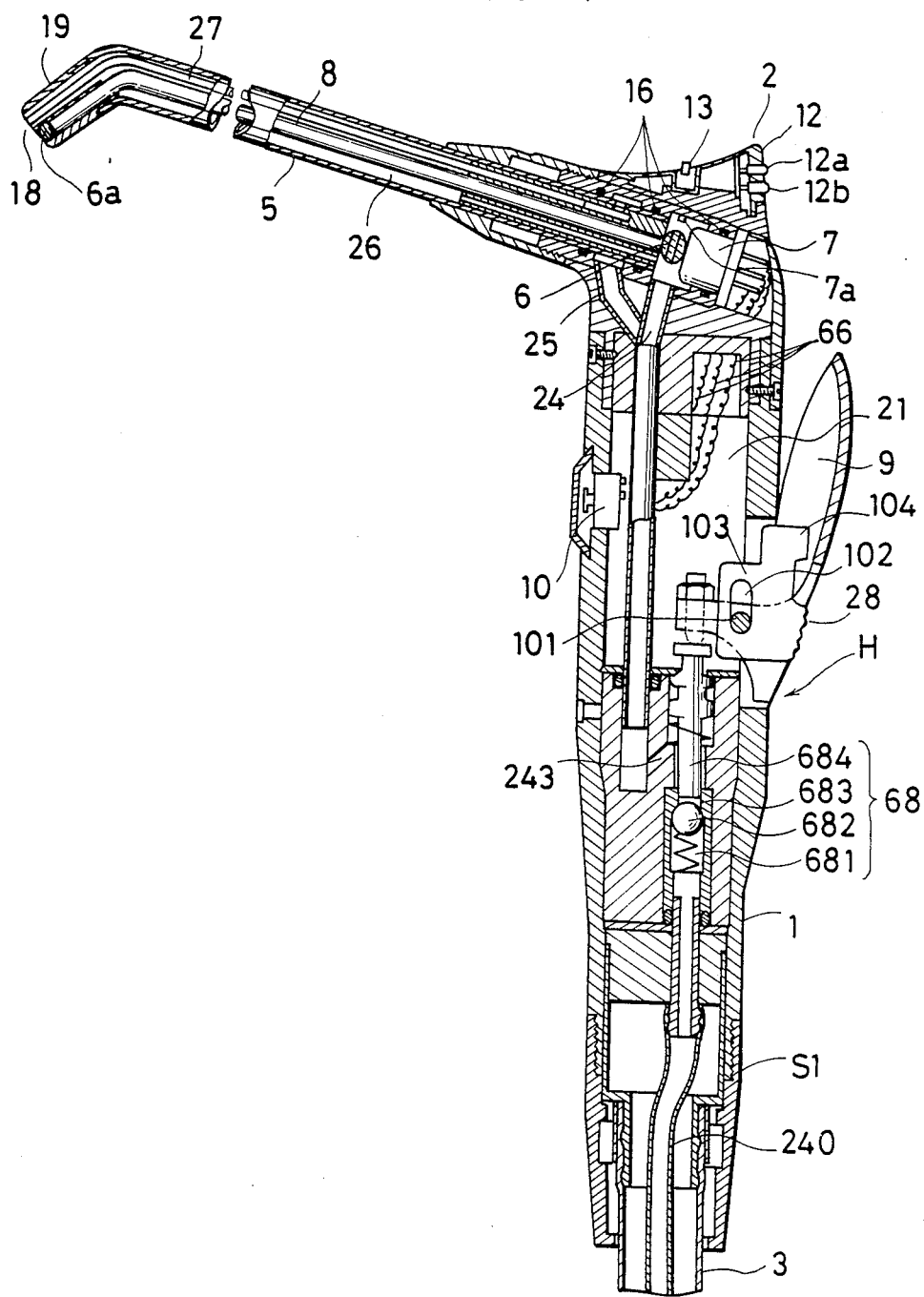
FIG. 4 is a vertical sectional side view illustrating a third embodiment of type I.

FIGS. 4 and 5 show a structure having additional functions by providing supply pipes 24, 25, 26 and 27 in the grip body 1 and the irradiation nozzle 5 in order to supply working media such as air A and water W from the connection hose 3 located at the lower end of the joint S1 to the body 1 and the irradiation nozzle 5. In this case, the lever 9 pivotably connected to the grip body 1 can be separated into an air supply lever 9a and a water supply lever 9b as shown in FIG. 5 so that the working media A and W supplied from the tube 3 connected at the lower end of the grip body can be supplied to the nozzle end port 18 or stopped by the hinge action of the corresponding supply control lever. More particularly, an air supply pipe 240 and a water supply pipe (not shown) disposed behind the air supply pipe are inserted into the sleeve joint S1 as shown in FIG. 4. These pipes are respectively connected to an air supply pipe 24 and a water supply pipe 25 in the grip body 1 via a valve mechanism 68 which functions interlocked with the control lever 9 and further connected to an air supply pipe 26 and a water supply pipe 27, both of which are built in the irradiation nozzle 5 along the axis of the nozzle 5. The water supply pipe 27 is extended to the end port 18 as a single pipe in the irradiation nozzle 5. The air supply pipe 26 extends along almost the entire length of the nozzle 5 and is tapered off concentrically with the outer wall of the pipe 27. Air and water supplied from the pipes 26 and 27 are partially combined at the end of the nozzle 5 to form mist and the mist can be irradiated from the end port 18 although there is no illustration to show how the mist is generated. The valve mechanism 68 described above has a valve mechanism which is opened or closed by the hinge action of the control lever 9. A ball valve 682 closes a valve plug 683 at all times by the spring 681. When the control lever 9 is pressed downward, a valve rod 684 moves downward and lowers the ball valve 682 to open the valve. As a result, air is supplied from a connection passage 243 to the air supply pipe 24. Water supply and stop can also be controlled in the same way as for air supply. Since the water supply/stop control mechanism is not shown in FIG. 4, water supply/stop control is not explained here. In the case of this structure, the irradiation switch 10 is disposed on the inward side of the body 1, unlike the embodiment shown in FIGS. 1, 2 and 3. The laser detector 7a is disposed away from the pipes 24 and 25.

When electric power is supplied from an electric power source (not shown) to the grip body 1 by operating the power switch S of the laser handpiece H having the structure described above, buzzer sound (irregularly continuous sound) is generated to notify that the handpiece H is on standby.

When the timer selection switch 13 disposed on the grip head 2 is set to a mode corresponding to the purpose of treatment, the selected setting mode is indicated by the timer indication 12b of the display means 12.

When the irradiation nozzle 5 is rotated around the head 2 so that the nozzle end port 18 is aligned to a treatment portion, and when the irradiation switch 10 is pressed and turned on by the hinge action of the control lever 9, the buzzer sound changes to intermittent sound to notify that the semiconductor laser generator 7 has been activated and laser has begun to be irradiated. The pilot lamp 12a on the display means 12 is turned on by a detection signal from the laser detector 7a.

The laser light generated from the semiconductor laser generator 7 is converged into a narrow beam by convergent lens 6, transmitted to the nozzle end port 18 via the laser light transmitting means 8 disposed in the irradiation nozzle 5 and further converged by the condenser lens 6a, then irradiated to a treatment portion.

Since the laser light from the semiconductor laser generator 7 is irradiated from the irradiation nozzle 5 which is connected to the grip head 2 at an angle, the operator of the handpiece can irradiate laser light to any treatment portion while gripping the grip body 1 without taking any unnatural posture. Therefore, treatment can be performed for a long time. The panel 12c of the display means 12 is positioned to face the operator during operation for treatment, the operator can check the indication of the display means 12 without changing the posture for treatment. In addition, the operator can confirm laser irradiation using the buzzer sound activated by the signal from the laser detector 7a. Therefore, the operator can safely continue treatment using the visual and aural functions.

In the case of the embodiment shown in FIGS. 1, 2 and 3, the irradiation switch 10 is automatically turned off when the operator releases the control lever 9. In the case of the embodiment shown in FIGS. 4 and 5, laser irradiation is stopped and the handpiece returns to the standby mode by turning off the irradiation switch 10.

When a laser light transmitting means such as an optical fiber is disposed in the grip head 2 along the axis of the irradiation nozzle 5 as shown in FIG. 3 and when a lighting means 23 comprising for example a halogen lamp is disposed at the position where the semiconductor laser generator 7 is disposed in the case of the embodiment shown in FIG. 1, the non-visible laser light can be traced completely by the lighting means 23 and higher treatment effect is assured at any treatment portion. If the lighting means 23 is used independently, any affected portion can be checked with the light regardless of laser irradiation.

In case when the supply pipes 24, 25, 26 and 27 for air A and water W are disposed in the grip body 1 and the irradiation nozzle 5 as shown in FIGS. 4 and 5, the handpiece H can have totally four treatment modes: laser irradiation from the semiconductor laser generator 7, air jet using air A, water jet using water W and mist spray of mixed air and water. Therefore, the handpiece H can be widely used as medical handpiece having many functions.

As described above, the medical laser handpiece of type I has the semiconductor laser generator in the grip head, and the irradiation nozzle is connected to the grip body at an angle so that laser light is irradiated to any treatment portion via the laser light transmitting means in the irradiation nozzle. Therefore, the operator can look at any affected portion and can accurately irradiate laser light to any treatment portion without positioning the grip body too close to the affected portion inside the mouth during treatment. The posture of the end port of the irradiation nozzle can be changed by turning the irradiation nozzle around the grip head when required. Furthermore, the irradiation nozzle can be removed to allow easy replacement with a new irradiation nozzle. When the irradiation nozzle is not used, laser light can be irradiated to a relatively wide area such as front teeth. Accordingly, the operator can easily treat teeth and periodontal sections in the mouth, which are difficult to be treated since they are relatively small and have complicated shapes. Thus treatment effect is greatly increased.

Figure 6:
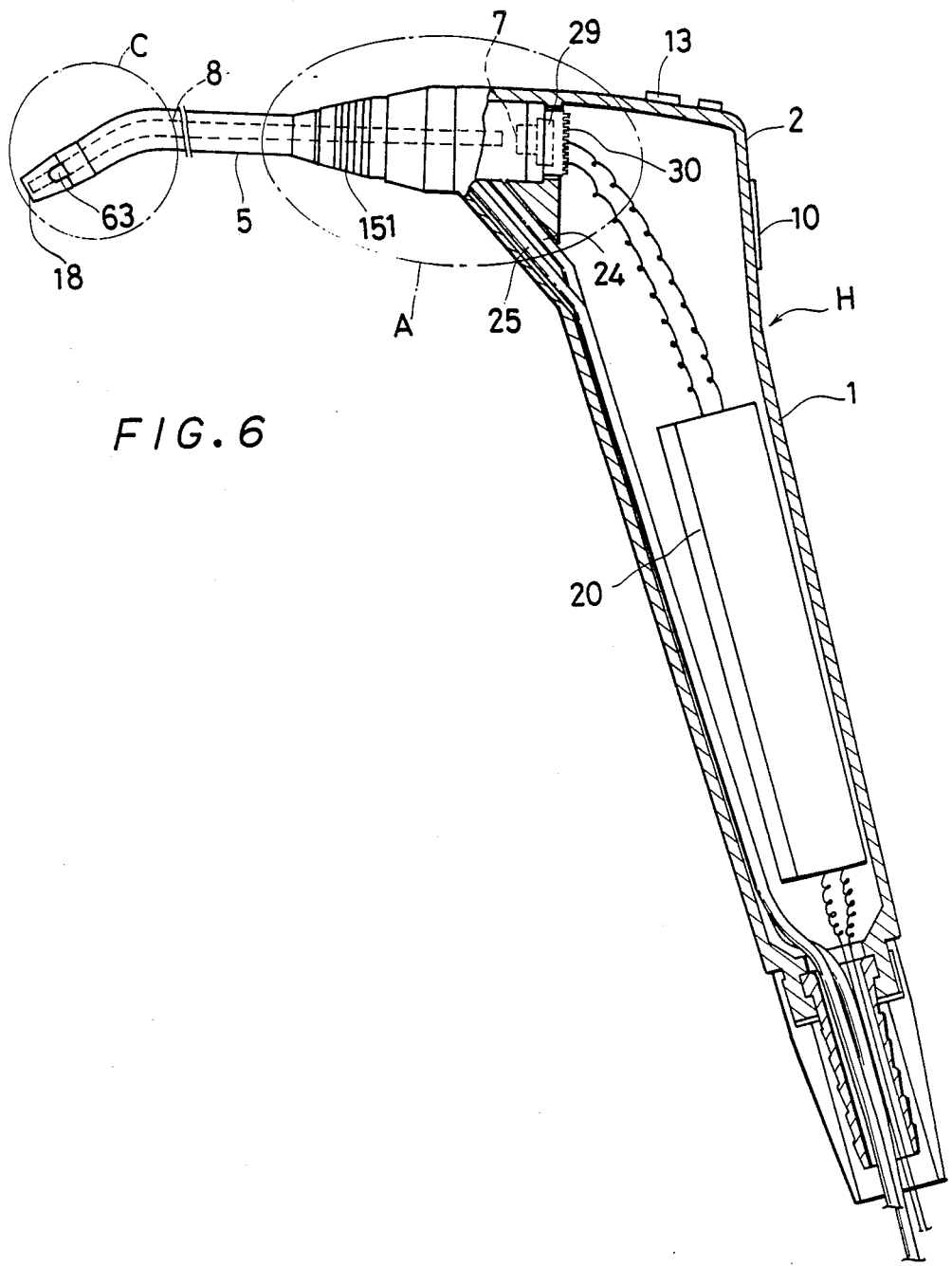
FIG. 6 is a vertical partially-sectional side view illustrating an embodiment of the laser handpiece of the present invention including types II, III and IV.

The laser handpiece types II, III and IV are explained next referring to FIGS. 6 to 11. For convenience of explanation, the numerals used in FIGS. 1 to 5 are also used to designated the identical members. The vertical partially-sectional side view of FIG. 6 shows the type which supplies air, water and mist of air and water into the grip body 1 and the irradiation nozzle 5 in the same way as shown in FIGS. 4 and 5. For convenience of explanation, the irradiation switch 10, control lever 9 and other parts included in the grip body 1 are not shown in FIG. 6. Referring to FIGS. 6 to 11, the members which are not shown in FIGS. 1 to 5 or replaced members are explained below.

The air supply pipe 24 and the water supply pipe 25 are disposed from the grip head 2 to the irradiation nozzle 5. The grip body 1 includes a control printed circuit board 20 to control the semiconductor laser generator 7. The control circuit board 20 is electrically connected to the semiconductor laser generator 7 which is included in the grip head 2.

Figure 7:
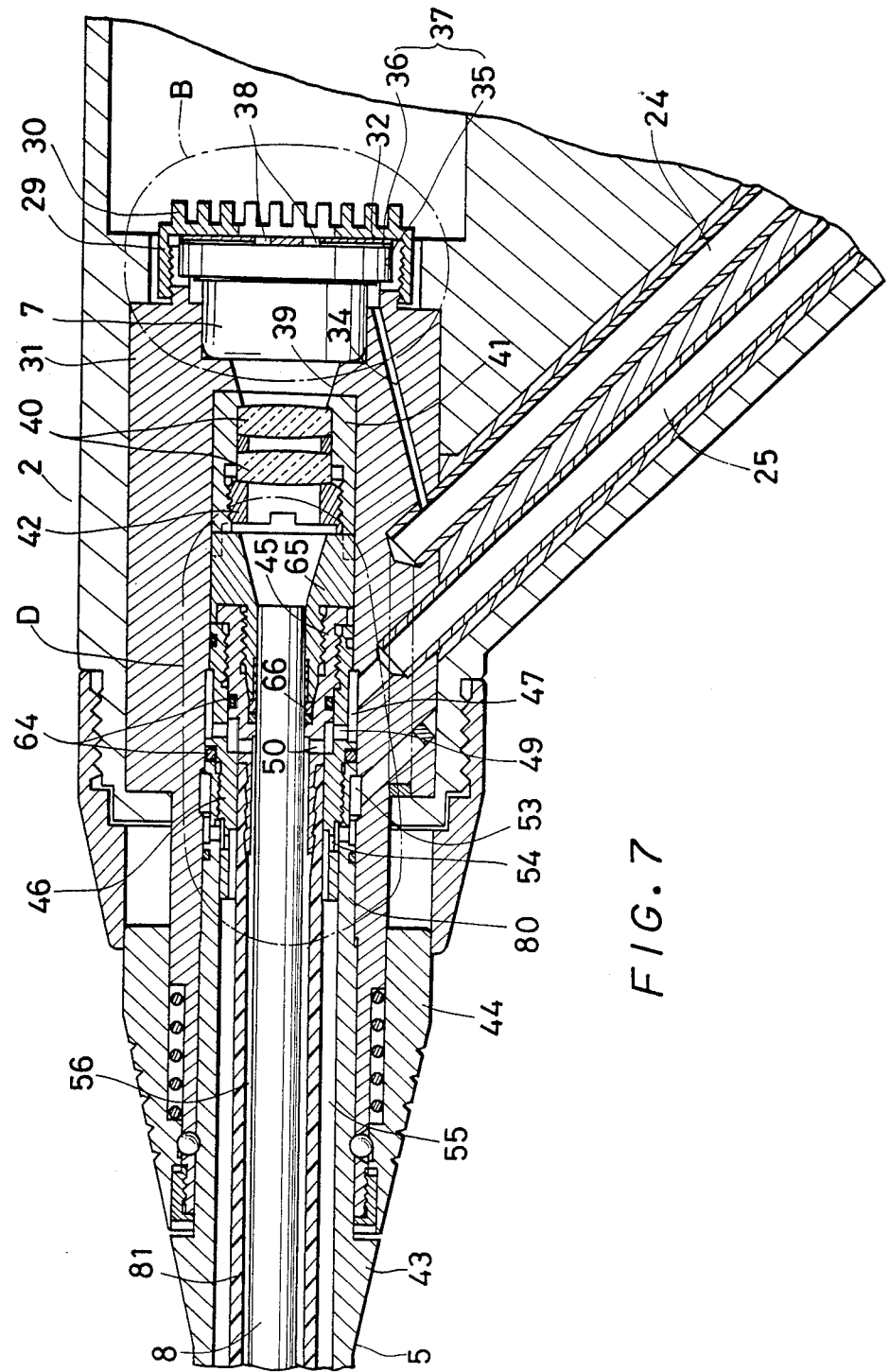
FIG. 7 is an enlarged vertical sectional view of section A of FIG. 6.
Figure 8:
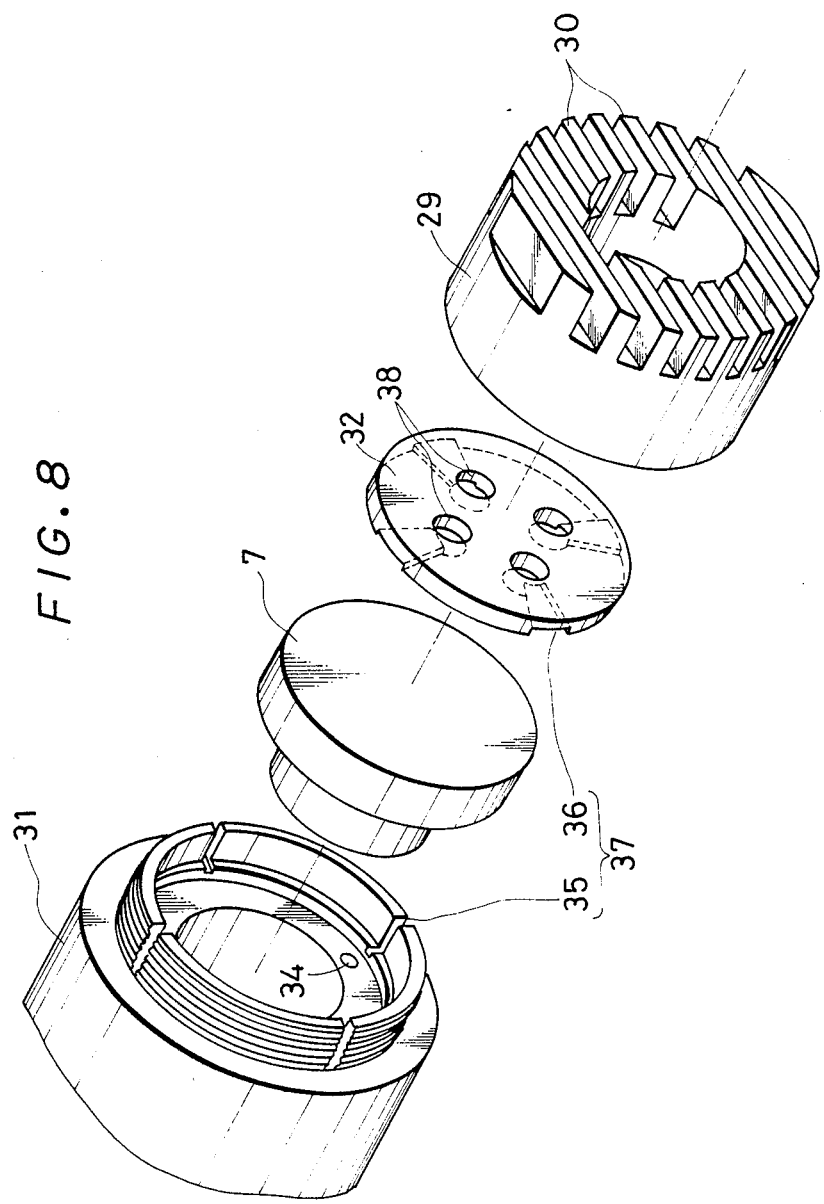
FIG. 8 is an exploded perspective view of section B of FIG. 7.

A tube-shaped inner case 31 is coaxially built in at the connection section of the grip head 2 and the irradiation nozzle 5 as shown in FIG. 7. At the base end section of the inner case 31, the semiconductor laser generator 7 is secured via a washer 32 by a threaded holding member 29 which has fins 30 at the rear end surface. In the inner case 31, the air supply pipe 24 and the water supply pipe 25 are built in. In addition, an air passage 34 with a small diameter is branched from the air supply pipe 24 to cool the semiconductor laser generator 7. Inside the semiconductor laser generator installation area of the inner case 31, slots 35 are formed as shown in FIG. 8. A plurality of grooves 36 are formed on the semiconductor laser generator 7 contacting the side of the washer 32. The cooling air supplied from the air supply pipe 34 enters around the rear surface of the semiconductor laser generator 7 through the slots 35 and the grooves 36. A clearance 37 provided to cool the semiconductor laser generator 7 is defined by the slots 35 and the groove 36. The small through holes 38 provided in the washer 32 are used to accommodate electric wires from the semiconductor laser generator 7.

The base end section of the inner case 31 has a tapered laser light receiving section 39, the diameter of which gradually decreases in the forward section. The tapered surface is goldplated or mirror-finished for total reflection so that the laser light from the semiconductor laser generator 7 can be transmitted without leakage. In adjacent to the light receiving section 39, optical lenses 40 are built in. Numerals 41 and 42 designate holding members used to secure the optical lenses 40 in place.

Figure 9:
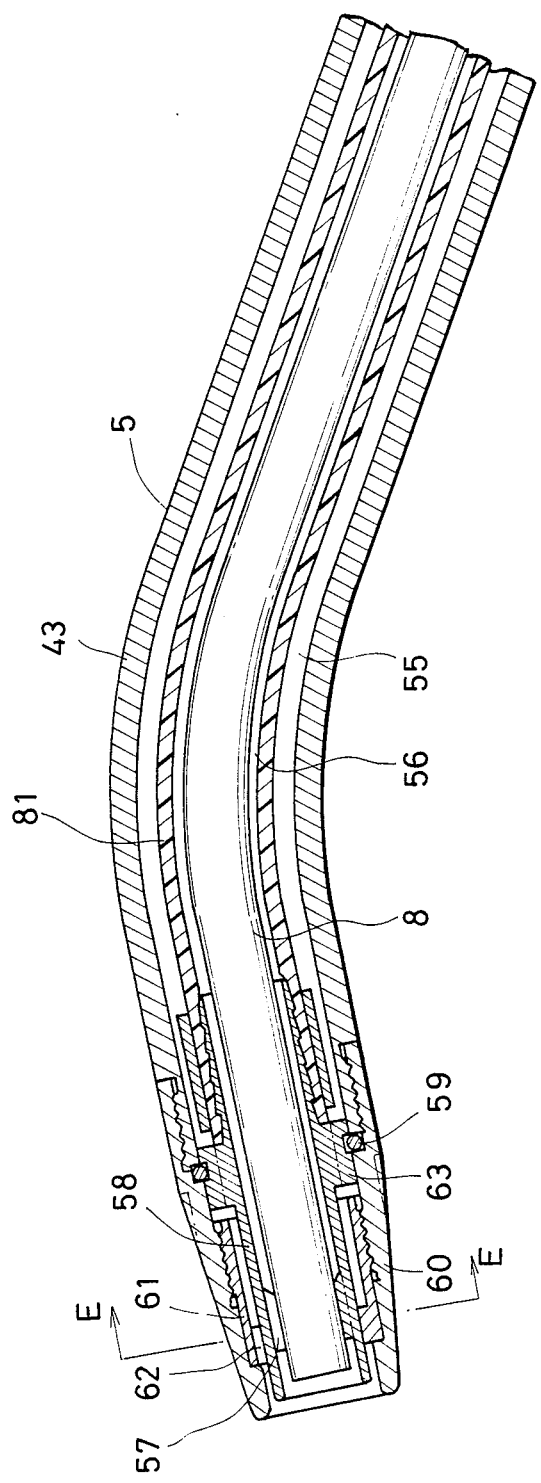
FIG. 9 is an enlarged vertical sectional view of section C of FIG. 6.

The irradiation nozzle 5 is basically composed of an outer shell 43, a laser light transmitting means or a glass fiber 8, which is inserted along the axis of the outer shell 43, and a flexible protection pipe 81 used to protect the fiber 8 as shown in FIG. 9. The base section 80 is formed to be a tube detachably inserted to the inner case 31 of the head 2 via the control sleeve 44. At the base end section 80, a joint 45 for the protection pipe 81, holding members 65 and 66 for combining the joint with the glass fiber 8 and a tightening member 46 for combining the joint 45 with the outer shell 43 are installed in place as shown in FIGS. 7 and 10. The holding member 65 also functions to transmit laser light coming from the optical lenses 40 to the glass fiber 8. The laser receiving section of the holding member 65 is gold-plated or mirror-finished and tapered off in the forward direction. The water supplied from the water supply pipe 25 passes through a circumferential groove 47 formed at the joint section between the grip head 2 and the irradiation nozzle 5, passage holes 49 and 50 provided in the tightening member 46 and the joint 45, enters the clearance 56 between the laser fiber 8 and the protection tube 81 and jetted out from the end of the nozzle while cooling the outer surface of the glass fiber 8. The air supplied from the air supply pipe 24 passes through a circumferential groove 53 and a passage hole 54 provided in the tightening member 46, enters a clearance 55 provided between the protection tube 81 and the outer shell 43 and jets out from the end of the nozzle 5 while cooling the outer surface of the protection tube 81.

The glass fiber 8 and the protection tube 81 are coaxially supported with the clearances 56 and 55 provided in the outer shell 43. At the end of the glass fiber 8, a joint 58 having a plurality of projections 57 provided inward is fit and connected to the protection pipe 81 as shown in FIGS. 9 and 11. The projections 57 contact the circumference of the glass fiber 8 to provide the clearance 56 between the glass fiber 8 and the protective tube 81. Cooling water jets out of the clearances between the projections 57. Around the joint 58, an end cap 60 is screwed and fit over the outer shell 43 via an open ring 59. Furthermore, a spacer member 61 is inserted between the end cap 60 and the joint 58 to provide an air exhaust passage. More particularly, projections 62 are provided at proper intervals on the inner circumferential surface of the end section of the spacer member 61 and contact the outer circumferential surface of the end section of the joint 58. A milled section 63 is formed around the outer circumferential surface of the joint 58, and the clearances 621 provided between the milled section 63 and the projections 62 of the spacer member 61 pass to the clearances 55. The air and water supplied from the air supply pipe 24 and the water supply pipe 25 cool the semiconductor laser generator 7, the glass fiber 8 and the protection tube 81 and jet out from the end of the irradiation nozzle 5 to cool a dental treatment portion or to perform functions required for treatment. Control valves for the working media (air and water) are disposed at the grip body 1 or at positions away from the nozzle 5 so that the operator can control such valves to jet out air, water or mist of air and water from the end of the nozzle 5 is required, in the similar way as a conventional dental three-way syringe. Numeral 64 designates an O-ring used to make joint sections airtight and watertight.

The shape of the clearance 37 is not limited to that shown in the figure. The present invention is applicable to handpieces having other shapes, and it is obvious that the structure of the handpiece of the present invention can be modified within the spirit and scope of the present invention.

Since type II of the laser handpiece of the above-mentioned embodiment has a function to air-cool the circumference of the semiconductor laser generator and has cooling fins on the semiconductor laser generator holding member, heat generation from the semiconductor laser generator is prevented and its output loss is reduced even when the semiconductor laser generator is built in such a limited space as the inside of a dental handpiece. Therefore, the output of the semiconductor laser generator can be increased effectively and this kind of handpiece can have a higher value in use.

With type III of the laser handpiece of the present invention, the treatment function using laser light is combined with a function to supply water, air or mist of air and water. By activating the working medium supply function during treatment using laser light, a treatment portion is cooled, the stimulation effect of laser light increases and an affected portion and surrounding area is cleaned, resulting in efficient treatment. When the mist is sprayed, the air jet encloses the water jet to ensure uniform misting. This further increases the cooling and cleaning functions of the handpiece. Furthermore, the laser fiber is surrounded by water and cooled to prevent heat generation and to reduce energy loss during transmission of the laser. For more convenience, the handpiece can also be used as a conventional three-way syringe when laser light is not used.

With type IV of the handpiece of the present invention, the light receiving section having a totally reflective taperedoff surface is provided between the semiconductor laser generator and the laser fiber. The laser generated by the semiconductor laser generator is thus totally reflected by the tapered surface and converged in the forward direction and almost 100% of laser light can enter the glass fiber. This reduces laser leakage and ensures effective treatment using laser light, depending on the output of the semiconductor laser generator. Moreover, heat generation due to laser leakage is not caused and instruments used around the handpiece are not adversely affected by heat generation due to laser leakage.

Accordingly, all or some of the structures of types II, III and IV should be preferably included in the laser handpiece of the present invention.

We claim:
1. A dental laser handpiece comprising:
a grip body;
a semiconductor laser generator disposed in said grip body;

an irradiation nozzle which is detachably connected to the head of said grip body at an angle to a longitudinal axis of said grip body and which includes a laser light transmitting means from said semiconductor laser generator, said semiconductor laser generator disposed on a longitudinal axis of said irradiation nozzle; and an irradiation switch which is disposed on said grip body, said semiconductor laser generator being disposed on the axis of said irradiation nozzle; and wherein said grip head is equipped with a lighting means and said laser light transmitting means is used to transmit illumination light from said lighting means disposed in said grip body and to also transmit laser light from said semiconductor laser generator disposed in said grip head;

a display means is provided on said grip head to indicate laser irradiation standby condition, laser irradiation condition and laser irradiation time selection modes; and air and water supply hose pipes are provided in said grip body, grip head and irradiation nozzle.

2. A medical laser handpiece according to claim 1, wherein said irradiation nozzle is equipped with a bent section at the end of said nozzle and said irradiation nozzle is rotatably connected to said grip head at the connection section of said nozzle.

3. A medical laser handpiece according to claim 1 or 2, wherein said semiconductor laser generator is secured to said grip head by a holding member equipped with cooling fins so that said semiconductor laser generator and surrounding area can be air cooled.

4. A medical laser handpiece according to claim 3, wherein an air supply pipe is built in said grip body and a clearance leading to said air supply pipe is formed between said grip body and said semiconductor laser generator.

5. A medical laser handpiece according to claim 3, wherein said holding member is made of a material having high thermal conductivity.

6. A medical laser handpiece according to claim 1 or 2, wherein said laser light transmitting means is inserted to a protection pipe with a water passing clearance provided between said laser light transmitting means and said protection pipe, and air passing clearances are provided between said protection pipe and said grip head and between said protection pipe and said irradiation nozzle so that water and air supplied through said water and air passing clearances can jet out of the end of said irradiation nozzle.

7. A medical laser handpiece according to claim 1 or 2, wherein a laser light receiving section having a total-reflection inner surface tapered off in the forward direction is disposed between said semiconductor laser generator and said laser light transmitting means.

* * * * *